United States Patent [19]

Keren

[11] Patent Number: 4,951,688

[45] Date of Patent: Aug. 28, 1990

[54] HYPERTHERMIC POWER DELIVERY SYSTEM

[75] Inventor: Hanan Keren, Kfar Saba, Israel

[73] Assignee: Elscint Ltd., Haifa, Israel

[21] Appl. No.: 400,716

[22] Filed: Aug. 30, 1989

[30] Foreign Application Priority Data

Sep. 1, 1988 [IL] Israel .......................... 87649

[51] Int. Cl.$^5$ .......................... A61N 5/02; A61B 5/055
[52] U.S. Cl. .................................. 128/804; 128/653 A
[58] Field of Search .................... 128/653 A, 399, 804, 128/422

[56] References Cited

U.S. PATENT DOCUMENTS

| | | | |
|---|---|---|---|
| 4,554,925 | 11/1985 | Young | 128/653 A |
| 4,798,209 | 1/1989 | Klingenbeck et al. | 128/804 X |
| 4,798,215 | 1/1989 | Turner | 128/804 |
| 4,815,479 | 3/1989 | Carr | 128/804 |

FOREIGN PATENT DOCUMENTS

| | | | |
|---|---|---|---|
| 0095124 | 11/1983 | European Pat. Off. | 128/653 A |
| 0219206 | 4/1987 | European Pat. Off. | 128/653 A |
| 3431314 | 3/1986 | Fed. Rep. of Germany | 128/804 |

*Primary Examiner*—Lee S. Cohen
*Attorney, Agent, or Firm*—Sandler, Greenblum & Bernstein

[57] ABSTRACT

A system for providing hyperthermic treatment of tumerous tissue using a phased array antenna for focusing radio frequency (RF) energy on the tumorous tissue. A magnetic resonance system generating free induction decay (FID) signals from the tumorous tissue. The FID signals are used to determine the relative phase and amplitude of RF excitations which are to be transmitted by each element of the phase array antenna.

7 Claims, 1 Drawing Sheet

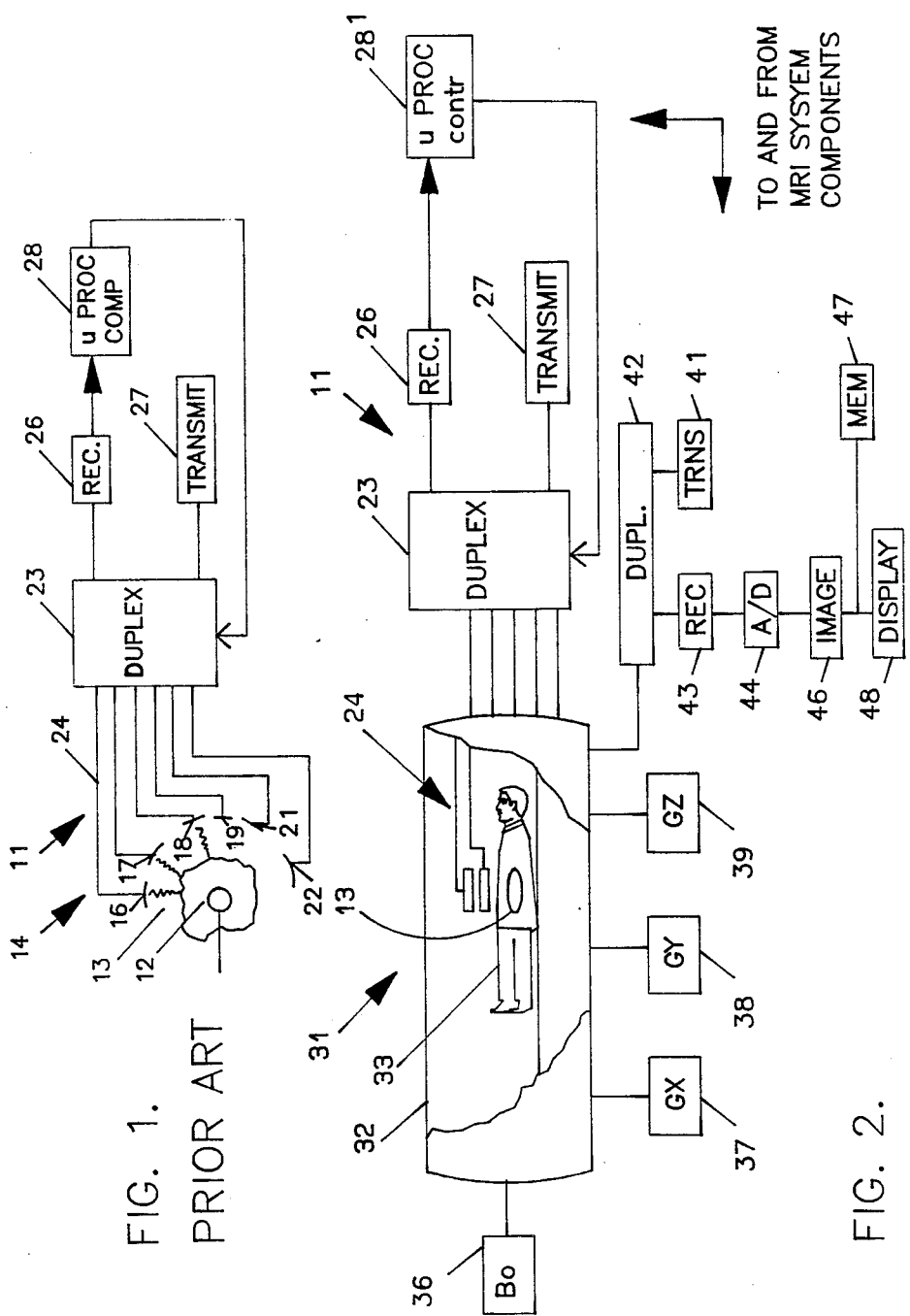

HYPERTHERMIC POWER DELIVERY SYSTEM

FIELD OF THE INVENTION

The invention is concerned with hyperthermia used in the treatment of cancer and more particularly with systems for selectively delivering hyperthermic power to tumorous tissue while avoiding healthy tissue. Tumorous tissue in general is surrounded by healthy tissue. It is essential that the healthy tissue not be damaged during the treatment designed to destroy the tumorous tissue.

BACKGROUND OF THE INVENTION

Electromagnetic heating has been used in the past for treating tumors. However, when the tumors are located deep within the body of the patient, it has been found to be very difficult to deliver sufficient hyperthermic energy to the tumorous tissue to destroy the tumorous tissue without adversely affecting surrounding healthy tissue or even healthy tissue in the path between the power source and the tumorous tissue. To avoid damage to healthy tissue, it is necessary to focus the microwave energy on the tumorous tissue. It has been found that it is very difficult to focus the microwave energy.

One solution has been to use phased-array antennas. Theoretically phased-array antennas can be used to actually focus the microwave energy for the heat treatment of the tumor without adversely affecting healthy tissue. The problem with the use of phased-array antennas is that it is necessary to determine the relative phase of excitation in each individual element of the array so that the electromagnetic energy is properly focused to the prescribed tumorous region. If the phased-array antennas were acting through a homogeneous medium then the phase determination could be accomplished by geometric computations. However, since the actual biological media through which the microwaves travel is far from homogeneous geometric computations are not practical. Such computations require the knowledge, along other things, of the exact tissue homogeneity distribution in the path of each ray from each array element. Accordingly, the solution has in the past been evasive.

The proposed solutions to the tissue inhomogeneity problems have included tissue temperature measurements on the tumor and surrounding tissue and conjugative methods. The temperature measuring methods include planting invasive temperature probes and using a feedback algorithm for varying the amplitude and/or phase outputs of the various array elements to maintain the tumor above a given temperature and the surrounding tissue below a given therapeutic temperature (42-44 degrees C. for example). See for example the articles entitled "Optical Temperature Control with Phased-Array Hyperthermia System" and "A Predictive Adaptive, Multipoint Feedback Controller for Local Heat Therapy of Solid Tumors" both published in the IEEE Transactions on Microwave Theory and Techniques", Vol. MTT-34, No. 5, May 1986.

Another solution proposed is the use of a probe invasively inserted into the patient juxtaposed to the tumor. See the article entitled: "Experimental Investigation of a Retro-focusing Microwave Hyperthermic Applicator: Conjugate Field Matching Scheme" written by J. Loane et al., and other articles published in the IEEE Transactions on Microwave Theory and Techniques, Vol. MTT-34 No. 5 May (1986). The invasive probe is used to transmit radio frequency or microwave energy. The phased-array antenna is used in this mode as a receiving antenna. The signals received by the phased-array antenna are analyzed to determine the phase and the amplitude of the received signal at each element relative to each of the other elements of the array. When focusing the microwave or radio frequency energy, the array elements are excited with energy that is proportional to the conjugate of the phase of the individual array elements in the receiving mode. By reciprocity the phase and amplitude of the radiated field from the array is thereby focused exactly at the tumor. Theoretically the method works regardless of the inhomogeneity of the medium through which the radio waves pass or differences between the array elements since the element differences and the inhomogeneity are cancelled out by the conjugate and reciprocity theorems. In both proposed solutions, however, hyperthermia treatment requires invasive means.

Accordingly, those skilled in the art are continuously searching for a means for focusing the radio frequency energy or microwave energy on to the tumorous tissue in a non-invasive manner. In addition, it is often not feasible to put a transmitter juxtaposed to the tumorous tissue. For example, when the tumorous tissue is in a critical area of a vital organ. Accordingly, those skilled in the art are seeking non-invasive methods of focusing the microwave or radio frequency energy used in hypothermic treatment of cancerous or tumorous tissues.

BRIEF DESCRIPTION OF THE INVENTION

In accordance with a preferred aspect or the present invention a system for providing hyperthermic treatment of tumorous tissue is provided, said system comprising a phased-array antenna for focusing radio frequency energy on the tumorous tissue to thereby heat and destroy the tumorous tissue, non-invasive means for transmitting radio frequency signals from the tumorous tissue, means responsive to said radio frequency signals for determining the relative phase and amplitude of radio frequency excitations to be transmitted by each element of said phased-array antenna, and means for transmitting radio frequency signals from each element of the said phased-array antenna using the determined radio frequency excitation.

In accordance with a feature of the present invention the non-invasive means for transmitting radio frequency signals from the vicinity of said tumor comprises a magnetic resonance system for generating free induction decay signals from the vicinity of said tumor or from the tumorous tissue itself.

In accordance with another feature of the invention the magnetic resonance system is used to cause echo signals to be transmitted from the tumorous tissue.

BRIEF DESCRIPTION OF THE DRAWINGS:

The above mentioned and other features and objects of the present invention will be best understood when considered in the light of the following description of a broad aspect of the present invention made in conjunction with the accompanying drawings, wherein:

FIG. 1 is prior art showing of a system for treating cancerous tissue with hyperthermia, and FIG. 2 is a block diagram showing of a system for providing hyperthermia treatment without resorting to the invasive placing of probes in the vicinity of the tumorous tissue and/or in the tumorous tissue.

GENERAL DESCRIPTION

FIG. 1 at 11 shows a prior art proposed system for hyperthermic treatment of cancerous tissue using a phased-array antennas. In is this system invasive techniques are necessary in order to place a transmitting probe in the tumorous tissue. The invasive probe is used in order to effectively determine the tissue density in the paths between each of the elements of the phased-array antenna and the tumor. Such a determination enables each of the elements to be energized in a manner so as to focus the radio frequency energy at the tumorous tissue without adversely affecting surrounding healthy tissue.

Those skilled in the art of fighting cancer have gone to great lengths to avoid invasive techniques. Thus, for example, one of the most popular methods of destroying cancerous tissue at the present time is through chemotherapy; where, chemical processes are used to selectively destroy the cancerous tissue without destroying the surrounding healthy tissue. There are many adverse and sometimes traumatic side effects, however, when using chemotherapy, which are well known. Nevertheless, chemotherapy is usually a preferred method rather than invasive methods. This, hyperthermia also would become an important weapon in the battle against cancer if some means could be provided whereby the destructive heat could be focused exclusively on the cancerous tissue without using invasive techniques. The prior art proposes the use of the invasive techniques, as shown in the hyperthermia system 11 of FIG. 1 wherein a probe or transmitting unit 12 is invasively placed juxtaposed to the cancerous tissue at 13. The probe or transmitter is activated by a radio frequency signal close to or at the same frequency as the hyperthermia causing radio frequency signal.

The phased-array antenna as shown at 14 has individual antenna elements, such as elements 16, 17, 18, 19, 21 and 22. The number of elements is not as important as the fact that there is an array of elements with each element used for transmitting a portion of the radio frequency or microwave energy to generate heat in the tumorous tissue and not in the surrounding tissue. Each of the elements is connected to a duplexer 23 through conductors such as conductors 24. The duplexer connects the elements to either a receiver 26 or radio frequency transmitter 27.

One of the problems with hyperthermia is that until now it has not been possible to determine the relative "weight" to apply to each of the antenna elements to focus the heat on a tumorous tissue. Thus, there is no way without using the invasive techniques of the prior art to know the phase and the amplitude of the signal to be applied to each of the elements of the phased-array antenna in order that the generated heat is effectively applied exclusively to the tumorous area. The prior art invasive method determines the amplitude and phase to be transmitted by each element through reliance on a conjugate field matching scheme. More particularly the prior art proposed transmitting from the tumorous area at a frequency close to the microwave frequency used for generating the heat for a very short period of time. The transmitted signals are received by the antenna elements and passed through the duplexer 23 to the receiver 26. The output of each of the signals from each of the elements is applied to the microprocessor computer 28. The microprocessor computer determines the total signal received and the phase and amplitude of the signal received by each of the elements 16, 17, 18, 19, 21 and 22. This enables computation of relative phase and amplitude of the signal for each element.

The relative phase and amplitude of each element is determined. Then in the transmitting mode this determined relative phase and amplitude is used to control the transmitted signal of each of the elements of the phased-array transducer. However, the big drawback of the prior art is that the transmitting probe is invasively placed in the patient.

FIG. 2 shows the present invention wherein an MR system 31 included in the hyperthermia system 11 is shown. The hyperthermia system is the same as that shown on FIG. 1 except no transmitting probe 12 is necessary. However, the duplexer 23, the receiver 26, transmitter 27 and the microprocessor computer 28 are all part of the inventive system. The microprocessor is indicated as 28' since it not only controls the hyperthermia system but also controls the MR system. An arrow 40 is shown directed to and from the microprocessor which indicates that it receives signals from the MR system and transmits signals to the MR system for controlling the MR process.

The magnetic resonance system 31 comprises a large magnet 32 for generating a static magnetic field. The large magnet 32 is sufficiently large to receive a patient 33 having tumorous tissue 13 within the bore of the magnet. The elements 24 of phased-array transducer are the same as that shown in FIG. 1 except that they are now located within the bore of the magnet juxtaposed to the patient as previously. The magnetic resonance system also includes a magnetizing current generator Ho shown at 36. As is well known the large static magnetic field is varied by gradient fields for purposes of locating the source of the free induction decay (FID) signals. Gradient fields are shown as generated by gradient field generators Gx indicated at 37, Gy indicated at 38 and Gz indicated at 39. The large static magnetic field aligns certain molecules (hereinafter called "spins") with the lines of force of the large static magnetic field that is typically assumed to be in the Z direction in an XYZ orthogonal coordinate system.

The aligned spins are "tipped" into the XY plane by a transmitted radio frequency pulse. The transmitted pulse is generated at RF transmitter 41 and sent through a duplexer 42 to radio frequency coils not shown in the large static magnet 32. The spins that are tipped into the XY plane generate the FID signals which are received by RF coils within the magnet 32. The receiving RF coils can be the same as the transmitting RF coils as can be understood from the use of the duplexer. The received FID signals (or echo signals depending upon the magnetic resonance sequence applied) that are detected by the RF coils are transmitted through the duplexer 42 to the receiver 43.

The received signal is an analog signal. It is sent through an analog to digital converter 44 and from there to an image processor 46. The image processor usually works in conjunction with an image processing memory 47 to provide an image for display unit 48. The RF tipping frequency and the gradient fields are manipulated to cause the FID or echo signals to emanate from the tumorous tissue 13. See for example U.S. Pat. No. 4,891,595, entitled "Restricted Volume Imaging" which issued on 2 Jan. 1990, which was filed in the United States on 26 May 1986, and which is assigned to the Assignee of this Application for precise procedures for exciting specified volumes to cause signals to be transmitted from those volumes. The location of the specified volume is verified by noting that the display is of the tumorous tissue showing that the received radio frequency signals are emanating from the tumorous tissue.

The RF phased-array antenna elements 24 pick up this signal, send it through duplexer 23 to the receiver 26. The received signals are then sent to the microprocessor controller 28' for computation of the relative phase and amplitude of the elements of the phased-array antenna. This information is sent to the duplexer 23 to control the phase and amplitude of the signal transmitted by each of the elements of the phased-array antenna 24. When the reciprocal of the amplitude and the conjugate of the phase of the relative received signal is transmitted as the hyperthermic signal then the hyperthermic signal focuses on the tumorous tissue 13 to heat that tissue destructively while the temperature of surrounding tissue is kept from rising unduly.

In operation then, the operator of the MR hyperthermic equipment first goes through a magnetic resonance scan sequence to obtain signals from the tumorous tissue. When the signals are obtained from the tumorous tissue the hyperthermic equipment determines the proper phase and amplitude to be to be applied to each element of the phased-array antenna in order to focus the RF signals on the tumorous tissue to generate destructive heat in the tumorous tissue. Note that in addition to other benefits the single microprocessor controller can be used for both the hyperthermic equipment and for the magnetic resonance equipment.

While the invention has been described with relation to a certain preferred embodiment it should be understood that this description is made by way of example only and not as a limitation on the scope of the invention, which is defined in the accompanying claims.

What is claimed is:

1. A hyperthermic power delivery system for providing hyperthermic treatment of cancerous tissue, said system comprising:
    a phased-array antenna including a plurality of antenna elements,
    non-invasive means for obtaining radio frequency (RF) signals from said cancerous tissue at said phased-array antenna,
    said non-invasive means for obtaining RF signals from said cancerous tissue at said phased-array antenna comprising a magnetic resonance system,
    means responsive to said obtained RF signals for determining the relative amplitude of excitation in each element of said phased-array antenna and the relative phase of the excitation received by each of the elements of the phased-array antenna, and
    means responsive to said determination for controlling the phase and amplitude of applied RF signals supplied to each element of said phased-array antenna in order to focus a transmitted RF signal to the cancerous tissue to exclusively, destructively heat the cancerous tissue.

2. The hyperthermic power delivery system of claim 1 wherein said magnetic resonance system comprises:
    a large magnet for receiving a patient with cancerous tissue therein and for aligning spins in said patient with the magnetic field of the magnet,
    means for generating gradient fields,
    RF coils operated responsive to RF pules for "tipping" said aligned spins to produce RF signals in the patient, and
    means for providing gradient and RF pulse sequences to obtain said produced RF signals from the cancerous tissue.

3. The hyperthermic power delivery system of claim 2 including means for rephasing said tipped spins which tend to dephase when tipped for obtaining echo signals from said cancerous tissue.

4. The hyperthermic power delivery system of claim 1 including means for obtaining images responsive to said obtained RF signals to thereby assure that the signals are coming from said cancerous tissue.

5. A method for delivering hyperthermic power to provide hyperthermic treatment of cancerous tissue, said method comprising the steps of:
    receiving radio frequency (RF) signals in a non-invasive manner from said cancerous tissue at elements of a phased-array antenna,
    said step of receiving RF signals in a non-invasive manner comprising receiving RF signals using magnetic resonance systems to obtain free induction decay (FID) signals from said cancerous tissue,
    calculating the relative amplitude and the relative phase of the received RF signals at each element of the phased-array antenna,
    using the calculated relative amplitude and phase for controlling the phase and amplitude of the RF signals transmitted by each element of said phased-array antenna in order to focus a transmitted RF signal on to the cancerous tissue to exclusively, destructively heat the cancerous tissue.

6. The method of claim 5 wherein said FID signals are echo signals.

7. The method of claim 5 including the step of using said received RF signals to provide an image of a patient, and using the image to assure that the signals are coming from said cancerous tissue.

* * * * *